United States Patent
Tao et al.

(10) Patent No.: US 12,239,640 B2
(45) Date of Patent: Mar. 4, 2025

(54) USE OF MILOXACIN IN PREPARATION OF MEDICINES FOR TREATING AND/OR PREVENTING DISEASES WITH T-TYPE CALCIUM CHANNELS AS THERAPEUTIC TARGET

(71) Applicant: SOOCHOW UNIVERSITY, Suzhou (CN)

(72) Inventors: Jin Tao, Suzhou (CN); Yuan Zhang, Suzhou (CN); Yufang Sun, Suzhou (CN); Xinghong Jiang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 792 days.

(21) Appl. No.: 17/430,655

(22) PCT Filed: Feb. 20, 2021

(86) PCT No.: PCT/CN2021/077075
§ 371 (c)(1),
(2) Date: Aug. 12, 2021

(87) PCT Pub. No.: WO2022/077823
PCT Pub. Date: Apr. 21, 2022

(65) Prior Publication Data
US 2022/0305002 A1    Sep. 29, 2022

(30) Foreign Application Priority Data
Oct. 13, 2020   (CN) .......................... 202011092544.7

(51) Int. Cl.
| A61K 31/4741 | (2006.01) |
| A61P 9/06 | (2006.01) |
| A61P 25/00 | (2006.01) |
| A61P 25/04 | (2006.01) |
| A61P 25/08 | (2006.01) |
| A61P 29/00 | (2006.01) |
| A61P 35/00 | (2006.01) |

(52) U.S. Cl.
CPC ............ *A61K 31/4741* (2013.01); *A61P 9/06* (2018.01); *A61P 25/00* (2018.01); *A61P 25/04* (2018.01); *A61P 25/08* (2018.01); *A61P 29/00* (2018.01); *A61P 35/00* (2018.01)

(58) Field of Classification Search
CPC ................................................ A61K 31/4741
USPC ....................................................... 514/271
See application file for complete search history.

(56) References Cited

U.S. PATENT DOCUMENTS

2018/0303948 A1*  10/2018  Birkett ................. A61K 31/407

FOREIGN PATENT DOCUMENTS

| CN | 1294519 A | 5/2001 |
| CN | 101553209 A | 10/2009 |
| CN | 102149282 A | 8/2011 |
| CN | 108472273 A | 8/2018 |

OTHER PUBLICATIONS

Yoshida et al., High-performance liquid chromatography with fluorescence detection for determination of miloxacin and its metabolite M-1 in fish, Bunseki Kagaku, vol. 55, No. 9, pp. 635-641 (Dec. 31, 2006).

Li et al., Spectral characteristic analysis and structural identification of miloxacin, Huaxue Shiji, 2016, 38(3), pp. 249-252.

* cited by examiner

*Primary Examiner* — Kahsay Habte
(74) *Attorney, Agent, or Firm* — SZDC Law PC (57) ABSTRACT

The invention discloses use of miloxacin in the preparation of medicines for treating and/or preventing diseases with T-type calcium channel as a therapeutic target. The invention discloses new use of miloxacin, which provides a new theoretical and technical support for developing medicines for treating and/or preventing diseases with T-type calcium channel as a therapeutic target, thus having a broad prospect of application in the field of clinical treatment.

10 Claims, 4 Drawing Sheets

USE OF MILOXACIN IN PREPARATION OF MEDICINES FOR TREATING AND/OR PREVENTING DISEASES WITH T-TYPE CALCIUM CHANNELS AS THERAPEUTIC TARGET

This application is the National Stage Application of PCT/CN2021/077075, filed on Feb. 20, 2021, which claims priority to Chinese Patent Application No. 202011092544.7, filed on Oct. 13, 2020 which is incorporated by reference for all purposes as if fully set forth herein.

FIELD OF THE INVENTION

The present invention relates to the technical field of biological medicines, and more particularly to use of miloxacin in the preparation of medicines for treating and/or preventing diseases with T-type calcium channels as a therapeutic target.

DESCRIPTION OF THE RELATED ART

Ion channels are a class of proteins on biological membranes that allow ions to pass through. They play an important role in sensory signal transduction, heart beat, smooth muscle peristalsis, and hormone secretion. Mutations at specific sites of ion channels will cause abnormal channel function and cell dysfunction, and ultimately lead to occurrence of diseases. In addition, some diseases may change the functions and structures of ion channels, resulting in compensatory ion channel diseases such as neuropathic pain.

Calcium ion channels are the most widely distributed and most abundant ion channels in the body. Among them, voltage-gated calcium channels are very important and can be divided into L-, P/Q-, N-, R- and T-types. The T-type calcium channels are low-voltage gated calcium channels, also known as Cav3 calcium channels, including subtypes Cav3.1, Cav3.2 and Cav3.3. The T-type calcium channel has a low activation threshold and a faster inactivation rate. It plays an important role in the regulation of neuronal excitation in the resting state, and has become an important target for drug action and development. The three subtypes of T-type calcium channels have similar structures, but have different current characteristics, distribution and physiological functions (Catterall W A et al., Pharmacol Rev, 2005, 57, 411-425). These different characteristics determine that the T-type calcium channels have diversity as drug targets.

On the one hand, the T-type calcium channels can be used as drug targets for pain treatment, mainly due to the following evidences and advantages. First, neuronal T-type calcium channels, especially the subtype Cav3.2, are expressed and distributed throughout the pain sensory conduction and sensing pathways, affecting the conduction of sensation (Zamponi, G W et al., Brain Res Rev, 2009, 60, 84-89). Knockdown or knockout of neuronal T-type calcium channel subtype Cav3.2 can lead to reduced sensitivity of animals to nociceptive stimuli (Bourinet E et al., Pain, 2016, 157, 15-22). Secondly, genetic or pharmacological inhibition of neuronal Cav3 current will inhibit the neuronal excitability, and enhancement of neuronal Cav3 current will increase the action potential firing. The above results indicate that Cav3 channels, particularly subtype Cav3.2, have an important physiological effect in pain, especially neuropathic pain and inflammatory pain.

On the other hand, T-type calcium channels can also be used as drug targets for the treatment of arrhythmia and other diseases (Mesirca P et al., Front Physiol, 2015, 6, 19). The subtype Cav3.1 distributed on Purkinje fiber cells, sinoatrial nodes and latent pacemaker cells affects the membrane potential level, triggers the local intracellular calcium release, activates the inward sodium-calcium exchange currents, and controls the cardiac electrical signal conduction and cardiac pacing. Studies have found that the current mediated by T-type calcium channels on the atrial pacemaker cells is of important physiological significance in maintaining the pacemaker cell repolarization, action potential initiation, and sinus node autonomy.

Moreover, the T-type calcium channels (mainly subtypesy Cav3.1 and Cav3.2) can also be used as drug targets for the treatment of excitatory neuropsychiatric disorders such as epilepsy (Zamponi G W et al., Pflugers Arch, 2010, 460, 395-403). Studies have found that mutations in the subtype Cav3.2 gene can increase the T-type calcium channel current, induce the neuronal excitation, and lead to epileptic seizures (Peloquin J B et al., Epilepsia, 2006, 47, 655-658). The use of selective T-type calcium channel blockers in the WAG/Rij rat model of epilepsy can effectively control epileptic seizures.

On the other hand, the T-type calcium channels can also be used as drug targets for the treatment of glioma, and the subtype Cav3.1 is abnormally expressed in glioma cells at a high level (Latour I et al., 2004, Glia, 48, 112-119). Studies have shown that the Cav3 channels, especially subtype Cav3.1, have an important regulatory effect on the growth, migration and differentiation of tumors, particularly gliomas. Inhibition of T-type calcium channels can significantly inhibit the growth of gliomas.

Miloxacin, one of the second generation of quinolone drugs, is widely used as a bactericidal drug in clinic. Miloxacin has a chemical name of 4-dihydrogen-1-ethyl-6, 7-methyleneoxy-4-quinolinone-3-carboxylic acid, a molecular formula of $C_{12}H_9NO_6$, a molecular weight of 263.2, and a chemical structure shown below:

Miloxacin is a powerful and broad-spectrum antibacterial drug widely used to treat bacterial infections. Previous studies have shown that miloxacin affects DNA synthesis by inhibiting the bacterial DNA gyrase, thereby exerting an antibacterial and anti-inflammatory effect. It can be used to treat prostatitis, enteritis, bacillary dysentery and biliary tract infections (Izawa A et al., Antimicrob Agents Chemother, 1980, 18, 41-44.). So far, there is no research and report on the use of miloxacin in the treatment of pain, arrhythmia, epilepsy and glioma.

SUMMARY OF THE INVENTION

To solve the above technical problem, an object of the present invention is to provide use of miloxacin in the preparation of medicines for treating and/or preventing diseases with T-type calcium channels as a therapeutic target. The present invention discloses new use of miloxacin, which provides a new theoretical and technical support for developing medicines for treating and/or preventing diseases with T-type calcium channel as a therapeutic target, thus having a broad prospect of application in the field of clinical treatment.

For the above purpose, the present invention provides use of miloxacin in the preparation of medicines for treating and/or preventing diseases with T-type calcium channels as a therapeutic target.

Preferably, the disease is inflammatory pain.

Preferably, the disease is neuropathic pain.

Preferably, the disease is arrhythmia.

Preferably, the disease is epilepsy.

Preferably, the disease is glioma.

Preferably, the T-type calcium channel is subtype Cav3.1 or subtype Cav3.2.

Preferably, miloxacin is used to inhibit T-type calcium channels.

Preferably, the medicine comprises miloxacin as an active ingredient, and also a pharmaceutically acceptable carrier.

Preferably, the dosage of the medicine is 40-50 nmol/kg body weight.

Compared with the prior art, the present invention has the following advantages and effects.

1. By studying the effect of miloxacin on T-type calcium channels, it is founded that miloxacin can significantly inhibit the currents of T-type calcium channels, especially subtypes Cav3.1 and Cav3.2, and the firing of neuronal action potentials. The present invention also proves through animal experiments that miloxacin can relieve the pain response in inflammatory pain and neuropathic pain by inhibiting T-type calcium channels, and has a good analgesic effect. By means of the inhibition of miloxacin on T-type calcium channels, miloxacin can be used in the preparation of medicines for the treatment and/or prevention of diseases with T-type calcium channels as a therapeutic target. These diseases also include arrhythmias, epilepsy, Glioma and so on.

2. The present invention discloses use of miloxacin in the preparation of medicines for treating and/or preventing diseases with T-type calcium channels as a therapeutic target, including inflammatory pain, neuropathic pain, arrhythmia, epilepsy, glioma and so on. The present invention also discloses the mechanism of action where miloxacin inhibits the currents of T-type calcium channels, especially subtypes Cav3.1 and Cav3.2. The present invention also discloses the dosage of the medicine.

BRIEF DESCRIPTION OF THE DRAWINGS

FIG. 1 shows the effects of miloxacin on the currents of T-type calcium channel subtypes Cav3.1, Cav3.2 and Cav3.3 in Example 1 of the present invention, in which FIG. 1A is a schematic view showing the currents of subtypes Cav3.1, Cav3.2 and Cav3.3 in the control group and the treatment group;

FIG. 1B is a histogram showing the currents of subtypes Cav3.1, Cav3.2 and Cav3.3 in the control group and the treatment group;

FIG. 1C shows an activation and a deactivation curve of subtype Cav3.1 current in the control group and the treatment group;

FIG. 1D shows an activation and a deactivation curve of subtype Cav3.2 current in the control group and the treatment group; and FIG. 1E shows a dose-effect curve of miloxacin in inhibiting the subtypes Cav3.1 and Cav3.2 currents.

FIG. 2 shows the effects of miloxacin on the T-type calcium channel current in Example 2 of the present invention, in which FIG. 2A is a schematic view showing the T-type calcium channel currents in the control group, the washout group and the treatment group;

FIG. 2B is a histogram showing the T-type calcium channel current density in the control group, the washout group and the treatment group; and FIG. 2C is a dose-effect curve of miloxacin in inhibiting the T-type calcium channel current.

FIG. 3 shows the effects of miloxacin on the firing of neuronal action potential in Example 3 of the present invention, in which FIG. 3A is a schematic view showing the neuronal firing in a 1-sec stimulation course in the control group and the treatment group; and FIG. 3B is a histogram showing the frequency of neuronal action potential in a 1-sec stimulation course in the control group and the treatment group.

FIG. 4 shows the effect of miloxacin on the pain behavior of CFA-induced inflammatory pain model rats in Example 4 of the present invention, in which FIG. 4A is a histogram showing changes in facial pain threshold over time in the solvent group and the treatment group;

FIG. 4B is a histogram showing changes in facial pain threshold over time in the saline group and the CFA model group;

FIG. 4C shows the effect of 10 nmol miloxacin administration group, 5 nmol miloxacin administration group and solvent group on the facial pain threshold of inflammatory pain model rats on day 2 after CFA induction; and FIG. 4D shows the effect of miloxacin administered 30 min later on the facial pain threshold of the inflammatory pain model rats on day 2 after CFA induction in the solvent group and the TTA-P2 group.

FIG. 5 shows the effect of miloxacin on the pain behavior of trigeminal neuropathic pain model rats in Example 5 of the present invention, in which FIG. 5A is a histogram showing the changes of facial pain threshold over time in the sham operation group and the CCI-ION model group;

FIG. 5B shows the effect of 10 nmol miloxacin administration group, 5 nmol miloxacin administration group and solvent group on the facial pain threshold of trigeminal neuropathic pain model rats on day 14 after the establishment of the CCI-ION model; and FIG. 5C shows the effect of miloxacin administered 30 min later on the facial pain threshold of trigeminal neuropathic pain model rats in the solvent group and the TTA-P2 group on day 14 after the establishment of the CCI-ION model.

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

Abbreviations involved in the description: DMSO: dimethyl sulfoxide; HEK293 cells: human embryonic kidney 293 cells; CFA: complete Freund's adjuvant; von Frey filament: filament pain threshold detector; DMEM: a medium containing various amino acids and glucose;

HEPES: 4-hydroxyethylpiperazinylethanesulfonic acid; EGTA: ethylene glycol diethyl ether diamine tetraacetic acid; and TTA-P2: 3,5-dichloro-N-[[4-fluoro-1-[[(4S)-tetrahydro-2,2-dimethyl-2H-pyran-4-yl]methyl]-4-piperidine]methyl]benzamide.

In the following examples, the solvent for miloxacin is DMSO.

Example 1. Effects of Miloxacin on the Currents of T-Type Calcium Channel Subtypes Cav3.1, Cav3.2 and Cav3.3 Transfected into HEK293 Cells In Vitro (1) Cell Transfection 1. Preparation before transfection: A flask of HEK293 cell culture was removed of the culture medium, and gently washed twice by adding 3 ml of a phosphate buffer. Then, the cells were digested by adding 1 ml of 0.25% trypsin, and pipetted by adding DMEM medium after 3-5 min to collect the cells. The cells were centrifuged at 1000 rpm for 5 min, and the supernatant was discarded. 5-10 ml of DMEM medium was added to suspend the cells. The cells were slowly pipetted again, then subcultured in a 35 mm petri dish covered with glass slides, and transfected after 24 h.

2. Transfection: The cells were transfected by liposome transfection, where the transfection reagent was Lipofectamine 3000, and the materials used: Cav3 plasmid 1.5 µg, transfection enhancement factor (TAG) 0.25 µg, and enhanced green fluorescent protein (EGFP) 0.1 µg. 48-72 h after transfection, the whole-cell patch clamp technique was used to record fluorescent HEK293 cells, with 9-12 cells per group.

The base sequences of Cav3.1, Cav3.2 and Cav3.3 plasmids were verified by gene sequencing and confirmed by DNA Star sequence analysis and alignment software that they are respectively consistent with the sequence Nos. NM_198376.3 (Cav3.1), NM_021098.3 (Cav3.2) and NM_021096.4 (Cav3.3) published in the NCBI database.

(2) Recording of Current

At room temperature, Multiclamp700B amplifier was used for whole-cell voltage clamp recording. The glass electrode was a drawn electrode, and the resistance of the electrode filled with intracellular fluid was 3-5 MΩ. DigiData1322A was converted into a digital signal in pClamp10.2 software. The series resistance compensation was 70-80%. The stimulating square wave was depolarized to −30 mV with a clamping voltage of −90 mV, and then returned to the clamping potential level. The current amplitude of the T-type calcium channel at this time was recorded.

Internal pipette solution: 110 cesium chloride, 4 magnesium-ATP, 0.3 sodium-GTP, 25 HEPES, 10 EGTA. External pipette solution: 5 barium chloride, 140 tetraethylamine chloride, 5 cesium chloride, 0.5 magnesium chloride, 5.5 glucose, 10 HEPES. The unit is mM, that is, millimoles/liter.

(3) Inhibition of Miloxacin on the Currents of T-Type Calcium Channel Subtypes Cav3.1, Cav3.2 and Cav3.3

The activation curve (I/Imax) and deactivation curve (G/Gmax) are commonly used indicators reflecting the degree of opening of voltage-gated ion channels. The dose-dependent relationship is an important indicator reflecting whether the compound has a pharmacological effect.

10 µM miloxacin was directly administered to the subtypes Cav3.1, Cav3.2 and Cav3.3 expressed on HEK293 cells, as the treatment groups. The groups before miloxacin administration were used as control groups.

Figure 1:
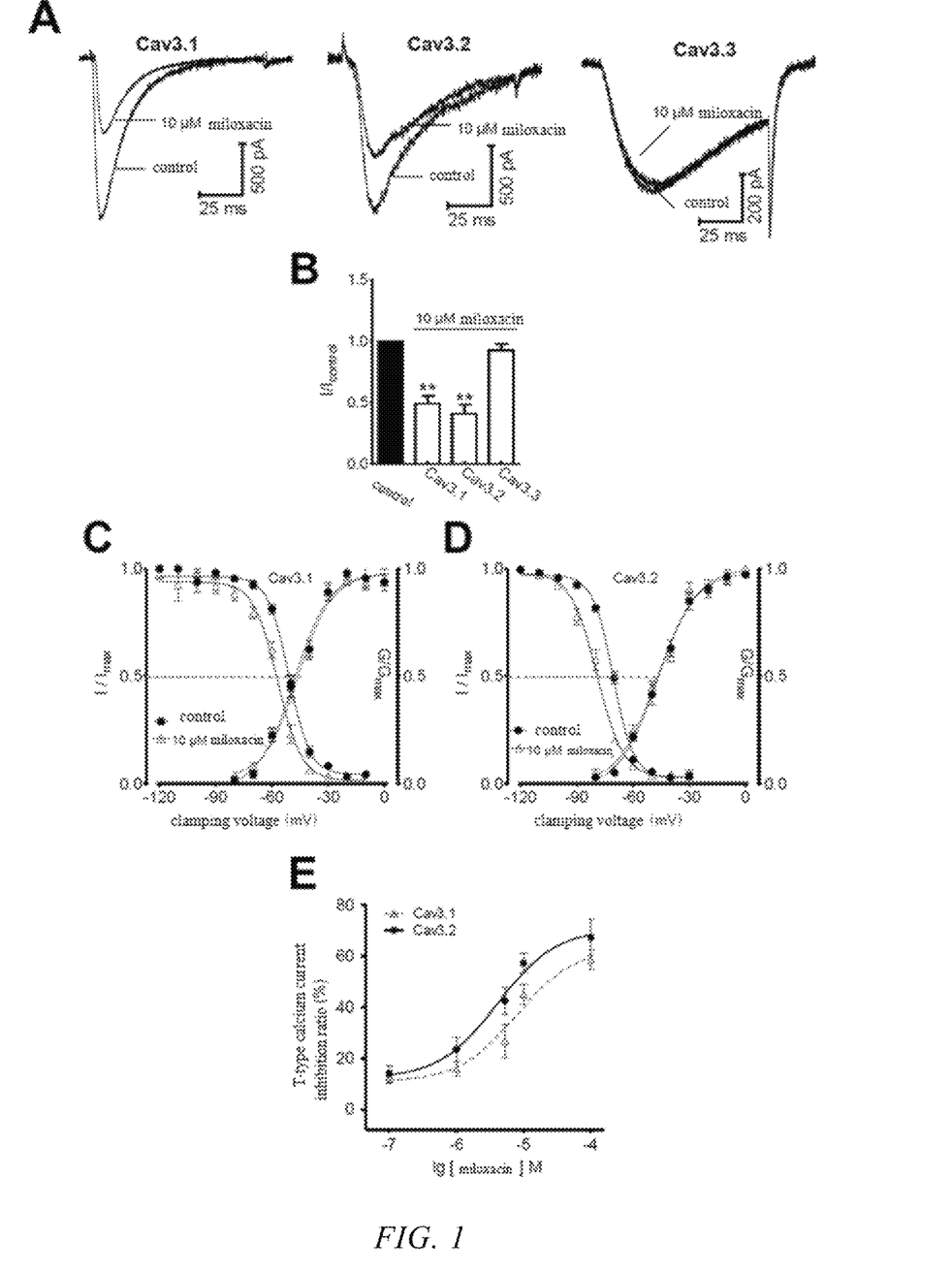

As shown in FIGS. 1A and 1B, compared to the control group, the subtype Cav3.1 current in the administration group is reduced by 49.6±2.9%, the subtype Cav3.2 current is reduced by 57.2±3.3%, and the subtype Cav3.3 current is only reduced by 2.1±0.7%. **p<0.01.

As shown in FIGS. 1C and 1D, compared to the control group, the inactivation constant $V_{1/2}$ of the subtype Cav3.1 in the treatment group is left shifted by 6.5±0.7 mV, and the inactivation constant $V_{1/2}$ of the subtype Cav3.2 is left shifted by 8.5±0.3 mV.

These suggest that miloxacin can accelerate the closing of T-type calcium channel subtypes Cav3.1 and Cav3.2, and left shift the conductivity-voltage relationship of the channel, thereby having an inhibitory effect on the currents of T-type calcium channel subtypes Cav3.1 and Cav3.2.

As shown in FIG. 1E, the inhibitory effect of miloxacin on inward currents of subtypes Cav3.1 and Cav3.2 is obviously dose dependent. The determination of the dose-dependent relationship is conventional. The $IC_{50}$ of miloxacin for subtype Cav3.1 current is 6.5±0.9 µM, and the $IC_{50}$ of miloxacin for subtype Cav3.2 current is 8.2±0.6 $IC_{50}$ is the half maximal inhibitory concentration.

The result shows that miloxacin can significantly inhibit the currents of T-type calcium channel subtypes Cav3.1 and Cav3.2.

Example 2. Effect of Miloxacin on T-Type Calcium Channel Current in Acutely Dissociated Primary Rat Trigeminal Ganglion Neurons (1) Dissociation of Trigeminal Ganglion Neurons Specifically, trigeminal ganglion neurons from adult male SD rats were acutely dissociated under the conditions of enzymatic hydrolysis of trigeminal ganglion neurons (Zhang Y et al., J Pineal Res, 2018, 64, e12476).

The trigeminal ganglia of male SD rats weighed about 220 g were exposed after anesthesia. The bilateral trigeminal ganglia were taken by using microscopic dissecting forceps, removed of their fiber connections, and then immediately placed in ice-cold oxygenated DMEM medium. The trigeminal ganglion in the culture medium was transferred into 3 mg/ml collagenase digestion solution, cut into pieces with microscissors, and digested at 37° C. for 45 min, and then digested in 2 mg/ml trypsin digestion solution for another 15 min. After the above operations, the digestion was terminated by adding DMEM medium containing 10% fetal bovine serum. The cells were dispersed by repeatedly pipetting, and filtered through a 40 µm cell sieve. The resulting suspension was centrifuged at 800 rpm for 3 min. After centrifugation, the supernatant was discarded, and the cell pellet was resuspended in DMEM medium. After resuspension, the cell suspension was seeded on a cover glass pre-coated with polylysine in a 24-well culture plate, and placed in an incubator at 37° C. with 5% $CO_2$ for later use.

(2) Recording of Current

The process was the same as that in Example 1.

(3) Inhibition of Miloxacin on T-Type Calcium Channel Current

10 µM miloxacin was directly administered to the T-type calcium channel in the trigeminal ganglion neurons as the treatment group. The group before miloxacin administration was used as a control group. An additional group that was washed off the drug before recording the current was used as the washout group.

Figure 2:
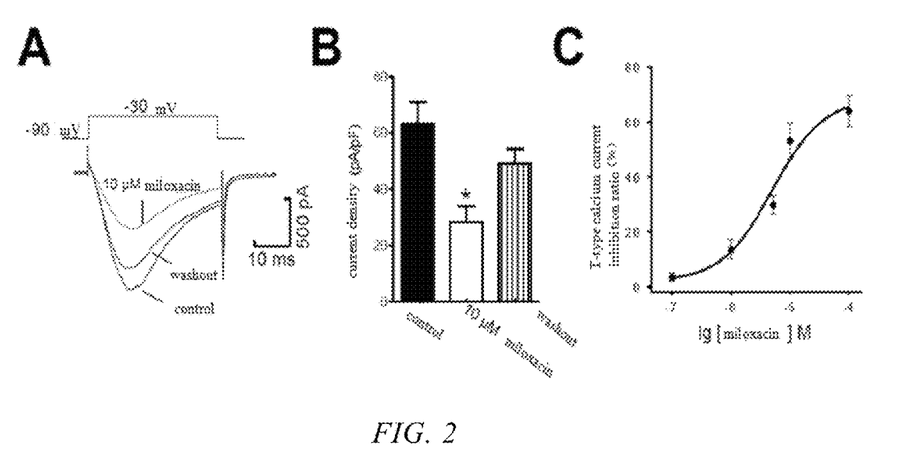

As shown in FIGS. 2A and 2B, compared to the control group, the T-type calcium channel current of the treatment group was reduced by 52.7±2.6%. *p<0.05.

As shown in FIG. 2C, the inhibitory effect of miloxacin on T-type calcium channel current is obviously dose dependent. The determination of the dose-dependent relationship is conventional. The $IC_{50}$ of miloxacin for T-type calcium channel current is 7.7±0.6 µM.

The results show that miloxacin can significantly inhibit the T-type calcium channel current.

Example 3. Effect of Miloxacin on Firing of Neuronal Action Potential of Acutely Dissociated Primary Rat Trigeminal Ganglion Neurons T-type calcium channel current is a low-voltage gated, rapidly activated and inactivated calcium ion current in neurons, which plays an important role in the repeated firing of neuronal action potentials.

(1) Dissociation of Trigeminal Ganglion Neurons

The process was the same as that in Example 2.

(2) Recording of Action Potential

At room temperature, Multiclamp 700B amplifier was used for whole-cell current clamp recording. A current of 180 pA was injected into the cell for 1 sec to stabilize the cell at −70 mV, and the frequency of the generated action potential was recorded.

Internal pipette solution: 10 sodium chloride, 110 potassium chloride, 2 EGTA, 25 HEPES, 0.5 sodium-GTP, 4 magnesium-ATP. External pipette solution: 2 potassium chloride, 128 sodium chloride, 2 calcium chloride, 2 magnesium chloride, 30 glucose, 25 HEPES. The unit is mM, that is, millimoles/liter.

(3) Inhibition of Miloxacin on the Firing of Neuronal Action Potential

10 µM miloxacin was directly administered to the T-type calcium channel in the trigeminal ganglion neurons as the treatment group. The groups before miloxacin administration were used as control groups.

Figure 3:
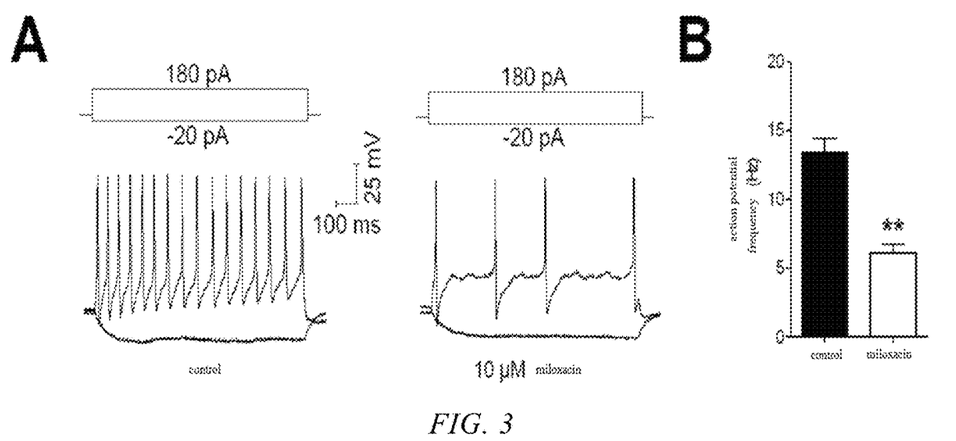

As shown in FIGS. 3A and 3B, the action potential of the control group is 13.3±1.5, and the action potential of the treatment group is 6.1±0.3. **p<0.01. The number of neuronal action potentials after administration of miloxacin decreases significantly.

The results show that miloxacin can significantly inhibit the firing of neuronal action potentials.

Example 4. Effect of Miloxacin on the Pain Behavior of CFA-Induced Inflammatory Pain Model Rats When the human body is stimulated by algesia, the nerve impulse generated by the excitation of algesireceptor will be transmitted to the trigeminal ganglion through peripheral sensory nerve fibers, then to the dorsal horn of the spinal cord after translocation, and then to the central part of the brain through an up-transmission pathway, thereby causing nociceptive feelings and pain. Primary afferent neurons receive pain afferents, and their soma gather to form the trigeminal ganglion. Therefore, trigeminal ganglion neurons are widely used as research objects for pain-related ion channel agonists or inhibitors.

The CFA-induced inflammatory pain model is one of the commonly used persistent inflammatory pain models, where obvious inflammation occurs at the site of CFA injection.

(1) Establishment of CFA-Induced Inflammatory Pain Model in Rats

Adult healthy male SD rats weighed 200-250 g were used. Before the experiment, the animals were allowed to acclimate to the breeding environment for three days. The model was established by a routine laboratory method. CFA was injected subcutaneously into the rat's facial whisker pad at a dose of 20 µl/mouse. Individuals with hyperalgesia and swelling of the footpad and ankle joint of right hind limb on day 2 after CFA injection were used as the experimental subjects, that is, the rats in the experiment group.

(2) Measurement of Facial Pain Threshold in Rats

Before the behavioral test, the rats were housed in a plexiglass box on a wire mesh frame to acclimate to the environment for three consecutive days, for 1 h each time. Test method: The middle part of the whisker pad was stimulated with von Frey filament at 1 g. If there were 3 escapes in 5 consecutive stimulations, the response was positive. Then, the same operation was repeated with von Frey filament at a lower level of intensity. If there was no positive response, the middle part of the whisker pad was stimulated with von Frey filament at a higher level of intensity. The minimum intensity at which a positive response occurs is taken as the facial pain threshold, that is, the facial mechanical pain threshold.

(3) Effect of Miloxacin on the Pain Behavior of CFA-Induced Inflammatory Pain Model Rats 1. Effect of miloxacin on the facial pain threshold of normal rats (without CFA induction): 20 normal rats were divided into two groups, each having 10 rats. The first group was a solvent group, and the second group was a treatment group. 10 nmol miloxacin was injected into the trigeminal ganglion of the second group of rats, and the corresponding solvent DMSO was injected into the trigeminal ganglion of the first group of rats.

Figure 4:
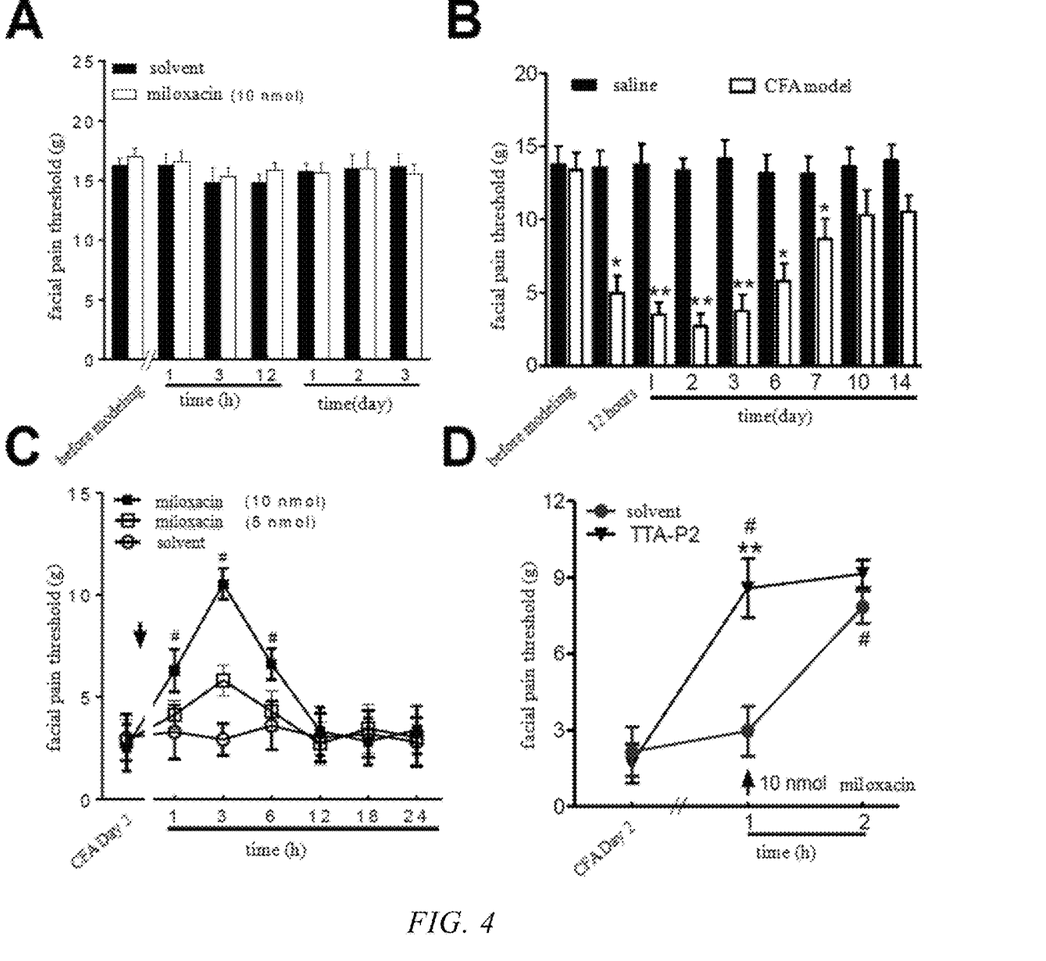

As shown in FIG. 4A, the facial pain thresholds of the rats in the solvent group and the treatment group are similar, and there is no significant difference.

It can be seen that the injection of 10 nmol miloxacin in the trigeminal ganglion does not affect the facial pain threshold of normal rats.

2. Effect of CFA induction on the facial pain threshold of rats: 20 normal rats were divided into two groups, each having 10 rats. The first group was a saline group, and the second group was a CFA model group. After 1d, 2d, 3d, 6d, 7d, 10d, and 14d, the facial pain threshold of each group was detected.

As shown in FIG. 4B, the facial pain threshold of the CFA model group on day 2 is 2.1±0.2 g, which is the lowest (*p<0.05, **p<0.01 vs. normal saline group). However, there is no significant change in facial pain threshold in the saline group.

It can be seen that CFA induction can lower the facial pain threshold of rats.

3. Effect of miloxacin on the facial pain threshold of CFA-induced inflammatory pain model rats: 27 rats with CFA-induced inflammation obtained by the above method were divided into three groups, each having 9 rats. On day 2 after CFA induction, 10 nmol miloxacin was locally injected into the trigeminal ganglion of rats in the first group, 5 nmol miloxacin was locally injected into the trigeminal ganglion of rats in the second group, and the corresponding solvent DMSO was locally injected into the trigeminal ganglion of rats in the third group. After 1 h, 3 h, 6 h, 12 h, 18 h, and 24 h, the facial pain threshold of each group was detected.

As shown in FIG. 4C, the facial pain threshold of the 10 nmol miloxacin group and the 5 nmol miloxacin group indicate significantly reversed mechanical hyperalgesia of rats with CFA-induced inflammation at 3 h after miloxacin administration (#p<0.05 vs. solvent group). That is, the facial pain threshold of rats rises.

It can be seen that local injection of miloxacin in the trigeminal ganglion can significantly alleviate the behavioral response to pain of CFA-induced inflammatory pain model rats, and has analgesic effect.

4. Study on the analgesic mechanism of miloxacin in CFA-induced inflammatory pain model rats: On day 2 after CFA induction, 2 nmol TTA-P2 was locally injected into the trigeminal ganglion, and then 10 nmol miloxacin was locally injected into the trigeminal ganglion after 30 min, which was used as the TTA-P2 group. The other group was injected with the corresponding solvent DMSO, and then administered with 10 nmol miloxacin by local injection 30 min later, which was used as the solvent group. TTA-P2 is a T-type calcium channel blocker, and the solvent for TTA-P2 is DMSO.

As shown in FIG. 4D, the local injection of TTA-P2 can increase the facial pain threshold of CFA-induced inflammatory pain model rats, and the following administration of miloxacin after the local injection of TTA-P2 does not further increase the facial pain threshold of CFA-induced inflammatory pain model rats, that is, there is no further analgesic effect. ** $p<0.01$ vs. day 2 after CFA induction +TTA-P2 group; #$p<0.05$ vs. solvent group at 1 h on day 2 after CFA induction. It can be seen that the analgesic effect of miloxacin on CFA-induced inflammatory pain model rats is achieved through the inhibition of T-type calcium channels.

The results show that miloxacin has analgesic effect on CFA-induced inflammatory pain model rats, and the analgesic mechanism is the inhibitory effect of miloxacin on T-type calcium channels.

Example 5. Effect of Miloxacin on the Pain Behavior of Trigeminal Neuropathic Pain Model Rats The trigeminal nerve is composed of peripheral processes from the trigeminal ganglion (TG), and includes three large branches, namely the ophthalmic nerve, the maxillary nerve and the mandibular nerve, which are distributed to different areas of the head and face. The trigeminal neuropathic pain model used in this study is a chronic constrictive injury to the infraorbital nerve (CCI-ION) model made to the left infraorbital nerve (the terminal branch of the maxillary nerve) via the oral cavity.

(1) Establishment of CCI-ION Model

Adult healthy male SD rats weighed 200-250 g were used. Before the experiment, the animals were allowed to acclimate to the breeding environment for three days. The rats were anesthetized with 4% chloral hydrate at an injection dose of 1 ml/100 g body weight. The tongue of the anesthetized rat in a supine position was pulled out and to the right to expose the left side of the mouth. At the level of the left maxillary first molar, a longitudinal incision of about 1 cm was cut along the gingival edge of the buccal aspect, and the tissue was bluntly isolated, to carefully expose the infraorbital nerve. The proximal and distal ends of the infraorbital nerve were loosely ligated with 5-0 suture, where the distance between the two ligatures was about 2 mm, and the tension was moderate. Ligation criteria: The diameter of the nerve was slightly reduced under the microscope, but the blood circulation in the outer membrane could not be arrested.

(2) Measurement of Facial Pain Threshold in Rats

The process was the same as that in Example 4.

(3) Effect of Miloxacin on the Pain Behavior of CCI-ION Model Rats

1. Effect of CCI-ION on the facial pain threshold of rats: 30 normal rats were divided into two groups, each having 15 rats. The first group is a sham operation group, and the second group is a CCI-ION model group. After 7d, 14d, 21d and 28d, the facial pain threshold of each group was detected.

Figure 5:
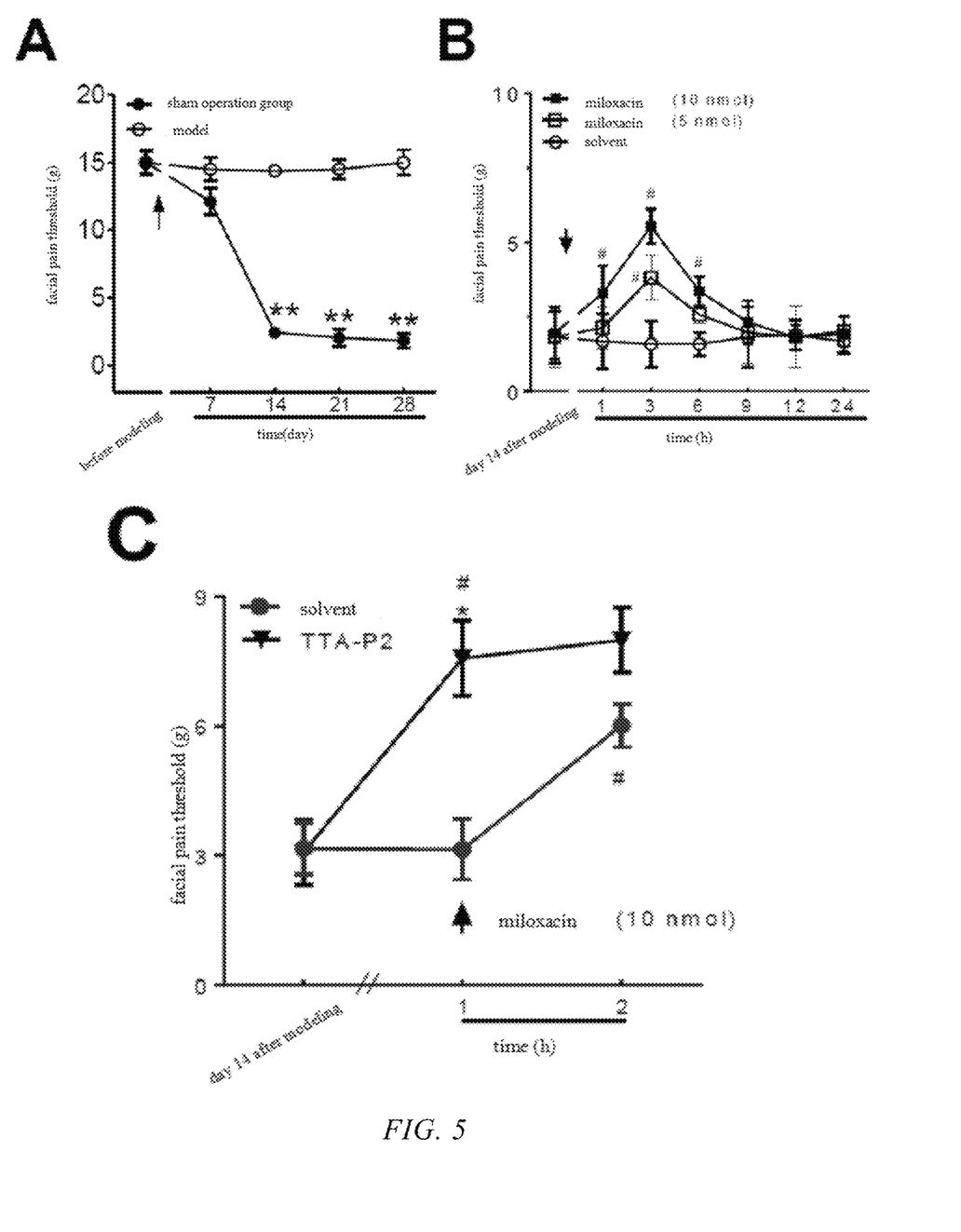

As shown in FIG. 5A, the facial pain threshold of the CCI-ION model group on day 14 was 2.6±0.3 g, which was significantly lowered (**$p<0.01$ vs. sham operation group). However, there is no significant change in facial pain threshold in the sham operation group.

It can be seen that CCI-ION can lower the facial pain threshold of rats.

2. Effect of miloxacin on the facial pain threshold of CCI-ION model rats: 27 CCI-ION model rats obtained by the above method were divided into three groups, each having 9 rats. On day 14 after the CCI-ION model was established, 10 nmol miloxacin was locally injected into the trigeminal ganglion of rats in the first group, 5 nmol miloxacin was locally injected into the trigeminal ganglion of rats in the second group, and the corresponding solvent DMSO was locally injected into the trigeminal ganglion of rats in the third group. After 1 h, 3 h, 6 h, 9 h, 12 h, and 24 h, the facial pain threshold of each group was detected.

As shown in FIG. 5B, the facial pain threshold of the 10 nmol miloxacin group and the 5 nmol miloxacin group indicate significantly reversed mechanical hyperalgesia of CCI-ION model rats at 3 h after miloxacin administration (#$p<0.05$ vs. solvent group). That is, the facial pain threshold of rats rises.

It can be seen that local injection of miloxacin in the trigeminal ganglion can significantly alleviate the behavioral response to pain of CCI-ION model rats, and has analgesic effect.

3. Study on the analgesic mechanism of miloxacin in CCI-ION model rats: On day 14 after the CCI-ION model was established, 2 nmol TTA-P2 was locally injected into the trigeminal ganglion, and then 10 nmol miloxacin was locally injected into the trigeminal ganglion 30 min later, which was used as the TTA-P2 group. The other group was injected with the corresponding solvent DMSO, and then administered with 10 nmol miloxacin by local injection 30 min later, which was used as the solvent group.

As shown in FIG. 5C, the local injection of TTA-P2 can increase the facial pain threshold of CCI-ION model rats, and the following administration of miloxacin after the local injection of TTA-P2 does not further increase the facial pain threshold of CCI-ION model rats, that is, there is no further analgesic effect.* $p<0.05$ vs. day 14 after model establishment +TTP-A2 group; #$p<0.05$ vs. solvent group at 1 h on day 14 after model establishment. It can be seen that the analgesic effect of miloxacin on CCI-ION model rats is achieved through the inhibition of T-type calcium channels.

The results show that miloxacin has analgesic effect in CCI-ION model rats, and the analgesic mechanism is the inhibitory effect of miloxacin on T-type calcium channels.

In the present invention, the effect of miloxacin on the currents of T-type calcium channel subtypes Cav3.1, Cav3.2 and Cav3.3 transfected into HEK293 cells in vitro is studied in Example 1 by using the whole-cell voltage clamp technology and current clamp technology. It is found that miloxacin can significantly inhibit the currents of T-type calcium channel subtypes Cav3.1 and Cav3.2. In Examples 2 and 3 of the present invention, the effect of miloxacin on the T-type calcium channel current and the firing of neuronal action potential in trigeminal ganglion neurons of rats is also studied. It is found that miloxacin can significantly inhibit the T-type calcium channel current and the firing of neuronal action potentials.

In the present invention, the effect of miloxacin on the pain behavior of CFA-induced inflammatory pain model rats is studied through animal experiments in Example 4. It is found that miloxacin has an analgesic effect on CFA-induced inflammatory pain, and the analgesic mechanism is the inhibitory effect of miloxacin on T-type calcium channels. In Example 5 of the present invention, the effect of miloxacin on the pain behavior of trigeminal neuropathic pain model rats was also studied. It is found that miloxacin has an analgesic effect on trigeminal neuropathic pain, and the analgesic mechanism is the inhibitory effect of miloxacin on T-type calcium channels.

In the present invention, it is found that miloxacin has an inhibitory effect on the currents of T-type calcium channels, especially the subtypes Cav3.1 and Cav3.2, and can also significantly inhibit the firing of neuronal action potentials. It is also found that miloxacin has obvious analgesic effects on both inflammatory pain and neuropathic pain, and the analgesic mechanism is the inhibitory effect of miloxacin on T-type calcium channels. Miloxacin has significant inhibition on T-type calcium channels, so it can be used in the preparation of medicines for the treatment and/or prevention of diseases with T-type calcium channels as a therapeutic target. These diseases also include arrhythmias, epilepsy, Glioma and so on.

The above-described embodiments are merely preferred embodiments for the purpose of fully illustrating the present invention, and the scope of the present invention is not limited thereto. Equivalent substitutions or modifications can be made by those skilled in the art based on the present invention, which are within the scope of the present invention as defined by the claims.

What is claimed is:

1. A method for treating a disease with T-type calcium channels as a therapeutic target, comprising:
   preparing a medicine using miloxacin; and
   treating a subject in need thereof with the medicine,
   wherein the miloxacin is directly administered.
2. The method according to claim 1, wherein the disease is inflammatory pain.
3. The method according to claim 1, wherein the disease is neuropathic pain.
4. The method according to claim 1, wherein the disease is arrhythmia.
5. The method according to claim 1, wherein the disease is epilepsy.
6. The method according to claim 1, wherein the disease is glioma.
7. The method according to claim 1, wherein the T-type calcium channels are subtype Cav3.1 or subtype Cav3.2.
8. The method according to claim 1, wherein miloxacin is used to inhibit the T-type calcium channels.
9. The method according to claim 1, wherein the medicine comprises miloxacin as an active ingredient, and also a pharmaceutically acceptable carrier.
10. The method according to claim 1, wherein the dosage of the medicine is 40-50 nmol/kg body weight.

* * * * *